United States Patent
Kim et al.

(10) Patent No.: US 9,204,443 B2
(45) Date of Patent: Dec. 1, 2015

(54) METHOD FOR CHANNEL SWITCHING IN WIRELESS PERSONAL AREA NETWORK AND APPARATUS FOR SAME

(75) Inventors: Suhwook Kim, Gyeonggi-Do (KR); Bonghoe Kim, Gyeonggi-Do (KR); Jaewon Lim, Gyeonggi-Do (KR); Junho Jo, Gyeonggi-Do (KR)

(73) Assignee: LG Electronics Inc., Seoul (KR)

( * ) Notice: Subject to any disclaimer, the term of this patent is extended or adjusted under 35 U.S.C. 154(b) by 108 days.

(21) Appl. No.: 14/008,612

(22) PCT Filed: Mar. 30, 2012

(86) PCT No.: PCT/KR2012/002406
§ 371 (c)(1),
(2), (4) Date: Oct. 7, 2013

(87) PCT Pub. No.: WO2012/134232
PCT Pub. Date: Oct. 4, 2012

(65) Prior Publication Data
US 2014/0023014 A1    Jan. 23, 2014

Related U.S. Application Data

(60) Provisional application No. 61/473,152, filed on Apr. 8, 2011, provisional application No. 61/472,594, filed on Apr. 6, 2011, provisional application No. 61/469,790, filed on Mar. 30, 2011.

(51) Int. Cl.
*H04W 72/04* (2009.01)
*H04W 36/06* (2009.01)
*H04W 48/16* (2009.01)
*H04W 84/10* (2009.01)
*A61B 5/00* (2006.01)

(52) U.S. Cl.
CPC .......... *H04W 72/0453* (2013.01); *H04W 36/06* (2013.01); *A61B 5/0024* (2013.01); *H04W 48/16* (2013.01); *H04W 84/10* (2013.01)

(58) Field of Classification Search
None
See application file for complete search history.

(56) References Cited

U.S. PATENT DOCUMENTS

| 7,092,428 B2 * | 8/2006 | Chen et al. ............ 375/132 |
| 2010/0097950 A1 * | 4/2010 | Jeon ............ 370/252 |
| 2010/0105332 A1 | 4/2010 | McHenry et al. |

(Continued)

FOREIGN PATENT DOCUMENTS

| EP | 2227046 A1 | 9/2010 |
| KR | 10-2009-0073774 A | 7/2009 |
| KR | 10-2010-0132978 A | 12/2010 |

OTHER PUBLICATIONS

Kim et al. "Multi-dimensional channel management scheme to avoid beacon collision in LR-WPAN". IEEE Transactions on consumer electronics, vol. 54, No. 2, May 2008.

(Continued)

*Primary Examiner* — Kerri Rose
(74) *Attorney, Agent, or Firm* — Morgan, Lewis & Bockius LLP

(57) ABSTRACT

A method for a user equipment switching an operation channel in a wireless personal area network (WPAN), disclosed in the present invention, comprises the following steps: setting a PAN coordinator and an association for a first frequency band; receiving from the PAN coordinator of the first frequency band information for channel switching to a second frequency band; and setting the PAN coordinator and the association for the second frequency band based on the switching information that is received.

5 Claims, 14 Drawing Sheets

(56) References Cited

U.S. PATENT DOCUMENTS

| | | | |
|---|---|---|---|
| 2011/0007727 A1 | 1/2011 | Driesen et al. | |
| 2011/0116490 A1* | 5/2011 | Wilhelmsson et al. | 370/343 |
| 2012/0106397 A1 | 5/2012 | Abedi | |
| 2013/0017791 A1* | 1/2013 | Wang et al. | 455/41.2 |
| 2013/0023215 A1* | 1/2013 | Wang | 455/41.2 |

OTHER PUBLICATIONS

Written Opinion and International Search Report issued in corresponding International Patent Application No. PCT/KR2012/002406 dated Oct. 18, 2012.

Search Report dated Mar. 20, 2015, issued by the European Patent Office in European Patent Application No. 12762837.8.

Cavalcanti et al., "Cognitive Radio based Wireless Sensor Networks," Computer Communications and Networks 2008, ICCCN '08, Proceedings of 17th International Conference, IEEE, Piscataway, NJ, USA, Aug. 3, 2008, pp. 1-6, XP031362211.

"IEEE Standard for Information Technology 1-15—Telecommunications and Information Exchange Between Systems—Local and Metropolitan Area Networks Specific Requirements Part 15.4: Wireless Medium Access Control (MAC) and Physical Layer (PHY) Specifications for Low-Rate Wireless Personal Area Networks (LR-WPANs)," IEEE Standard 802.15.4-2003, IEEE, New York, USA, Jan. 1, 2003, pp. 1-670, XP017603617.

* cited by examiner

| Frame control | Sequence Number | Addressing Fields | Auxiliary Security Header | SuperFrame Specigication | GTS fields | Pending address fields | Beacon Payload | FCS |

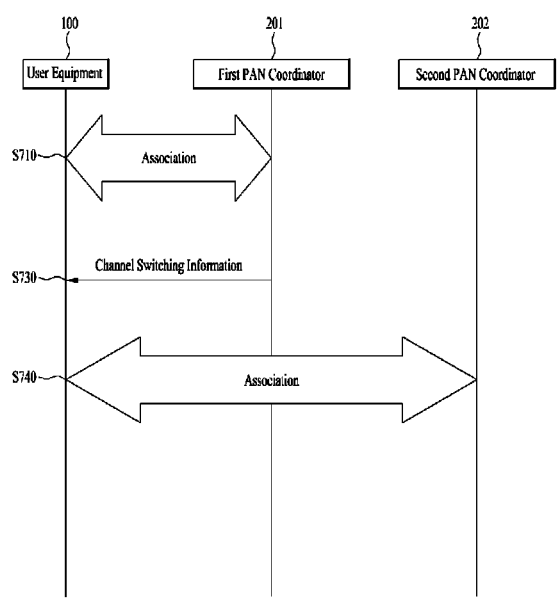

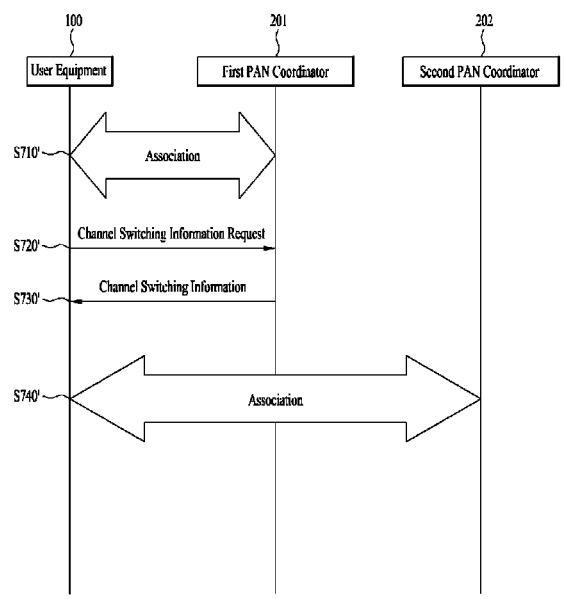

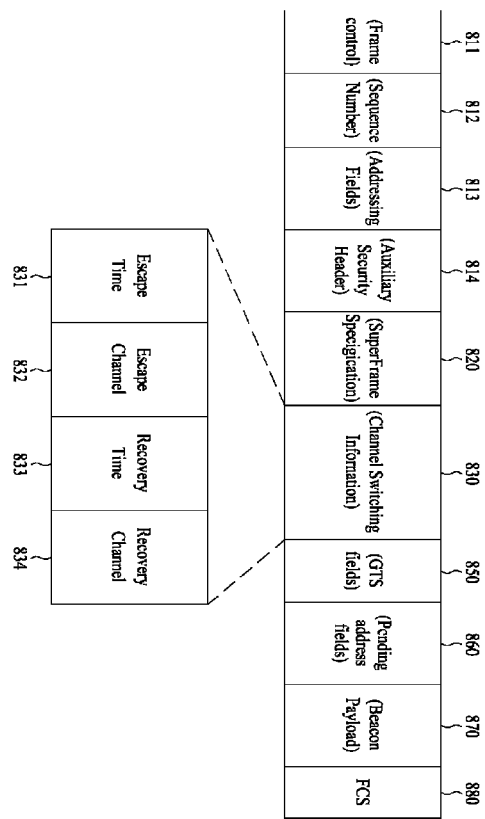

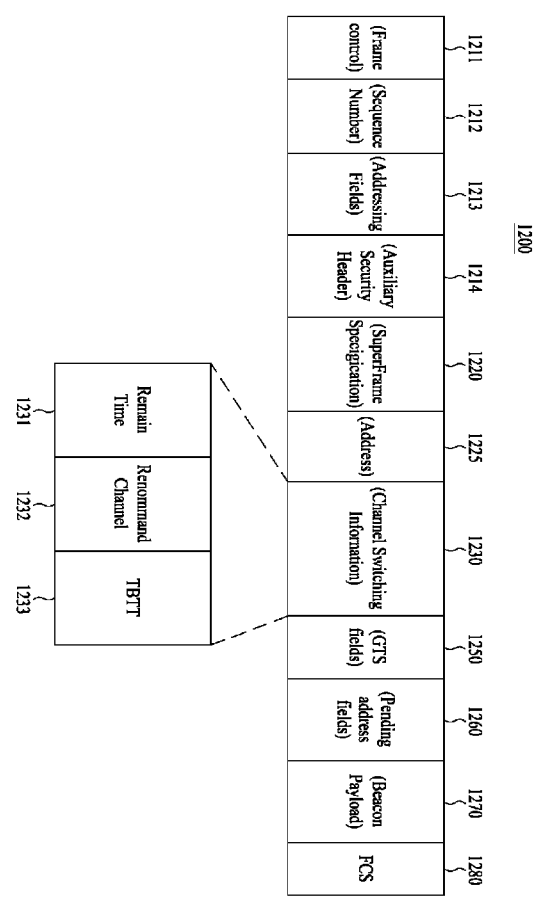

ically designed to provide a flexible platform for supporting a wire-
METHOD FOR CHANNEL SWITCHING IN WIRELESS PERSONAL AREA NETWORK AND APPARATUS FOR SAME

TECHNICAL FIELD

The present invention relates to a method of a channel switching in a WPAN system and an apparatus therefor, and more particularly, to a method of switching to a different channel, which is switched by an MBAN user equipment and an apparatus therefor.

BACKGROUND ART

Personal portable devices can perform a communication by constructing low-rate wireless personal area networks (hereinafter abbreviate LR-WPAN).

As an example of the LR-WPAN, there is a network following IEEE 802.15.4 standard. IEEE 802.15.4 standard provides transmission speed of 20 Kbps and 40 Kbps in 868/915 MHz band using BPSK (binary phase-shift keying) and provides the transmission speed of 250 Kbps in 2.45 GHz band using O-QPSK (offset quadrature phase-shift keying). IEEE 802.15.4b standard provides transmission speed of 250 Kbps in 868/915 MHz band using the O-QPSK as well.

An MBAN (medical body area network) system, which is one of the networks following IEEE 802.15.4 standard, is designed to provide a flexible platform for supporting a wireless networking of a plurality of sensors used to monitor physiological data of a patient in such a healthcare facility as a hospital.

The MBAN system operates in 2360 MHz~2400 MHz bands based on IEEE 802.15.4j and a maximum emission bandwidth of the MBAN system is limited to 5 MHz.

In case of operating in 2360~2390 MHz, a transmit power of the MBAN system corresponds to a smaller value among 1 mW and 10*log(B) dBm. In this case, B corresponds to 20 dB emission bandwidth. In case of operating in 2390~2400 MHz, the transmit power of the MBAN system corresponds to a smaller value among 20 mW and 10*log(B) dBm. In this case, B corresponds to 20 dB emission bandwidth.

2360~2400 MHz band is a frequency band already assigned to a different wireless communication system. The MBAN system operates based on a radio cognitive technology. The radio cognitive technology means a communication technology performed by adaptively changing such a transmission/reception property as a frequency band, transmit power, a coding scheme, and the like in a manner that a network or a radio communication device actively detects and judges a surrounding communication environment for an optimized communication. In this case, if a radio cognitive device detects a use of a different licensed user (primary user) in a frequency band of which the radio cognitive device intends to use, to operate in a manner of not interfering the communication of corresponding users is the first priority.

To this end, in case of operating in 2360~2390 band, the MBAN devices should operate in an indoor of a registered healthcare facility. In particular, a use of 2360~2390 MHz band should be controlled by a cooperation with the different licensed user. If the different licensed user uses the corresponding band, all operations in the corresponding band are initialized and should be resumed by newly using 2390~2400 MHz band. In some cases, operations can be resumed not by using 2390~2400 MHz band but by moving to a different channel in 2360~2390 MHz.

If the MBAN devices move to an outdoor, the MBAN devices stop operating or should transmit in a manner of changing a transmission band to 2390~2400 MHz, which is used as a basic band. In case of operating in 2390~2400 MHz band, the MBAN devices can be used irrespective of whether the MBAN devices are positioned at the indoor or the outdoor.

In a legacy MBAN system, in case that the aforementioned specific situation occurs, a method of switching a channel used in a prescribed band among 2360~2390 MHz band and 2390~2400 MHz band to a channel of a different band is not defined yet.

DISCLOSURE OF THE INVENTION

Technical Task

Accordingly, an object of the present specification is to provide a method of switching a channel for the MBAN and an apparatus therefor.

Technical Solution

According to one embodiment of the present specification, a method of switching an operation channel, which is switched by a user equipment in a WPAN (wireless personal area network) system is disclosed. The method includes the steps of establishing an association with a PAN (personal area network) coordinator of a first frequency band, receiving information on a channel switching to a second frequency band from the PAN coordinator of the first frequency band, wherein the information on the channel switching includes a time for switching to the second frequency band and channel information, and establishing an association with a PAN coordinator of the second frequency band based on the received switching information, wherein the first frequency band and the second frequency band are classified on the basis of whether the user equipment can preferentially use a frequency of a corresponding band.

The first frequency band may correspond to a frequency band between 2360 MHz and 2390 MHz and the second frequency band may correspond to a frequency band between 2390 MHz and 2400 MHz.

The channel switching may occur when a different wireless communication system uses the first frequency band or the user equipment moves to an outside of a designated area.

The information on the channel switching to the second frequency band may further include a PAN ID of the PAN coordinator operating on a channel of the second frequency band to switch.

The information on the channel switching to the second frequency band may further include a time for switching back to the first frequency band after switching to the second frequency band and channel information.

The step of receiving the information on the channel switching to the second frequency band from the PAN coordinator of the first frequency band may correspond to a step of receiving via a beacon frame. Or, the step of receiving the information on the channel switching to the second frequency band from the PAN coordinator of the first frequency band may correspond to a step of receiving via a command frame including the channel switching information.

The method may further include the step of requesting the information on the channel switching to the second frequency band to the PAN coordinator of the first frequency band.

After the step of establishing the association with the PAN coordinator of the second frequency band, the method may further include the steps of receiving information to switch to the first frequency band from the PAN coordinator of the second frequency band and establishing an association with the PAN coordinator of the first frequency band based on the received information.

The information to switch to the first frequency band can include a time for switching to the first frequency band, a channel to switch, and information on a beacon frame transmission time on the channel to switch.

The step of receiving the information to switch to the first frequency band from the PAN coordinator of the second frequency band may correspond to a step of receiving via a beacon frame.

According to a different embodiment of the present specification, a user equipment in a WPAN (wireless personal area network) system is disclosed. The user equipment includes a control unit configured to control a channel switching of the user equipment and a radio communication unit configured to communicate with a PAN (personal area network) coordinator according to a control of the control unit.

The control unit is configured to control the radio communication unit to establish an association with a PAN coordinator of a first frequency band, the control unit is configured to control the communication unit to receive information on a channel switching to a second frequency band from the PAN coordinator of the first frequency band, wherein the information on the channel switching includes a time for switching to the second frequency band and channel information, the control unit is configured to control the radio communication unit to establish an association with a PAN coordinator of the second frequency band based on the received switching information, wherein the first frequency band and the second frequency band are classified on the basis of whether the user equipment can preferentially use a frequency of a corresponding band.

The information on the channel switching to the second frequency band can include a time for switching to the second frequency band and channel information.

The information on the channel switching to the second frequency band may further include a PAN ID of the PAN coordinator operating on a channel of the second frequency band to switch.

After establishing the association with the PAN coordinator of the second frequency band, the control unit is configured to control the radio communication unit to receive information to switch to the first frequency band from the PAN coordinator of the second frequency band and the control unit is configured to control the radio communication unit to establish an association with the PAN coordinator of the first frequency band based on the received information.

Advantageous Effects

According to embodiment of the present invention, an MBAN system can efficiently perform a communication without conflicting with a different radio communication system. Hence, an MBAN user equipment and a PAN coordinator can more stably communicate with each other.

DESCRIPTION OF DRAWINGS

FIG. 7a and FIG. 7b is a flowchart for a method of a channel switching, which is switched by a user equipment according to embodiment of the present invention;

FIG. 8a to FIG. 8d is a diagram of channel switching information according to one embodiment of the present invention;

FIG. 12a and FIG. 12b is a diagram of a delivery message of channel switching information according to a different embodiment of the present invention;

BEST MODE

Mode for Invention

Figure 1:
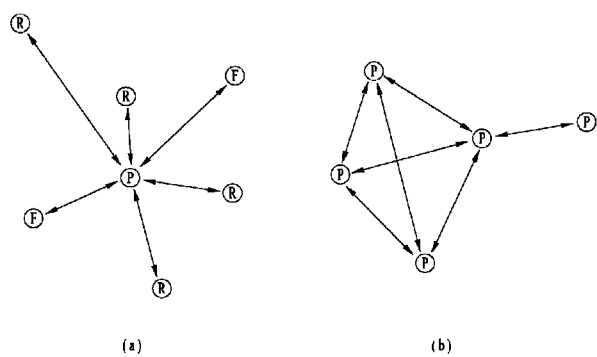
FIG. 1 is a diagram of a network topology based on IEEE 802.15.4.

The technical terminologies used in the present specification are used only to describe a specific embodiment(s) and have no intention to restrict the present invention. The technical terminologies used in the present specification should be construed not as excessively inclusive meanings or excessively reduced meanings but as meanings generally understood by those having ordinary skill in the technical field, to which the present invention pertains, unless defined as other meanings especially in the present specification. If the technical terminologies used in the present specification fail in correctly representing the idea of the present invention, they should be substituted with technical terminologies correctly understandably by those having ordinary skill in the technical field to which the present invention pertains. Moreover, general terminologies used by the present invention may be construed not as the excessively reduced meanings but as the meanings defined in dictionaries or the sequence of the context.

And, the singular number representation used in the present specification may include the plural number representation unless mentioned clearly and differently in context. In the present application, such a terminology as 'configured', 'include' and the like should be construed not as necessarily including various components or steps written in the present specification but as including the components or steps in part or further including additional components or steps.

Moreover, Suffixes 'module' and 'unit' for a component used in the present specification are given or used interchangeably in consideration of facilitation in preparing the specification only but do not have meanings or roles different from each other.

Moreover, a terminology, each of which includes such an ordinal number as $1^{st}$, $2^{nd}$ and the like, may be used to describe various components. In doing so, the various components should be non-limited by the corresponding terminologies, respectively. The terminologies are only used for the purpose of discriminating one component from other components. For instance, a $1^{st}$ component may be named a $2^{nd}$ component while coming within the scope of the appended claims and their equivalents. Similarly, the $2^{nd}$ component may be named the $1^{st}$ component.

In the following description, a preferable embodiment according to the present invention is explained in detail with reference to the attached drawings. The same reference numbers will be used throughout the drawings to refer to the same or like parts in this specification irrespective of the sign of the drawings and the overlapped explanation on the corresponding content can be omitted.

And, in describing the present invention, if the detailed description of the related art is determined as making the point of the present invention unclear, it will be omitted. The accompanying drawings, which are included to provide a further understanding of the invention and are incorporated in and constitute a part of this specification, illustrate embodiments of the invention and together with the description serve to explain the principles of the invention only. While the present invention has been described and illustrated herein with reference to the preferred embodiments thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

Embodiments disclosed in the present specification can be supported by standard documents for a system according to IEEE 802.15.4, which is a low-rate wireless personal area network. Or, the embodiments can be supported by standard documents disclosed for at least one of IEEE 802 system, 3GPP system, 3GPP LTE and LTE-A (LTE-advanced) system, and 3GPP2 system. In particular, steps or parts not explained to clearly reveal the technical idea of the present invention among the embodiments disclosed in the present specification can be supported by the aforementioned documents. And, all terminologies disclosed in the present specification can be explained by the standard document.

In the following description, embodiments of the present specification are explained centering on IEEE 802.15.4 standard, by which the technical idea of the present invention disclosed in the present specification may be non-limited to this.

FIG. 1 is a diagram for an example of a network topology following IEEE 802.15.4 standard.

In a network according to IEEE 802.15.4 standard, two types of device can participate in the network. The two types of device may include a full function device (hereinafter abbreviate FFD) and a reduced function device (hereinafter abbreviate RFD). Hence, a topology of a network according to IEEE 802.15.4 can be determined according to a function of devices participating in the network. FIG. 1 (a) is an example of a star topology and FIG. 1 (b) is an example of a peer-to-peer topology.

Since the FFD is a device capable of performing full functions, for instance, the FFD can perform a communication with the FFD or the RFD and can perform such a function as a network initialization, a node management, node information storage, and the like. In particular, among the FFDs, the FFD enabling different devices to construct a network is called a personal area network (PAN) coordinator device (hereinafter abbreviate coordinator). Hence, the aforementioned network topology can be constructed by the FDD playing a role of the coordinator.

Yet, the RFD performs a function less than the function capable of being performed by the FFD. In particular, a counterpart device with which the RFD performs a communication is limited to the FFD. Hence, the RFD cannot play a role of the coordinator. Hence, the RFD can have a small size of stack structure in a manner of taking complete charge of a network function to the FFD and can save a calculation/memory resource. In particular, the RFD transmits a data in a manner of searching for the coordinator. After transmitting the data, the RFD immediately terminates an access to the coordinator and can enter into a save (sleep) mode. Hence, the RFD has a very low quantity of power consumption and can operate for a long time with a battery power.

Referring to FIG. 1, a device represented as 'F' indicates the FFD, a device represented as 'R' indicates the RFD, and a device represented as 'P' indicates the FDD playing a role of the coordinator.

In the star topology depicted in FIG. 1 (a), a communication between a device and a coordinator is performed only. In this case, the device is a starting point or an ending point of the communication. On the other hand, the coordinator may become the starting point, the ending point, or a router.

In the peer-to-peer topology depicted in FIG. 1 (b), each device can communicate with any different device in a network. Hence, such a more complex form of a network as a mesh network can be constructed.

The star network can manage devices to make a battery life last for a longtime and the peer-to-peer network has high data reliability and high access recognition rate since the peer-to-peer network can construct one or more data delivery paths.

Figure 2:
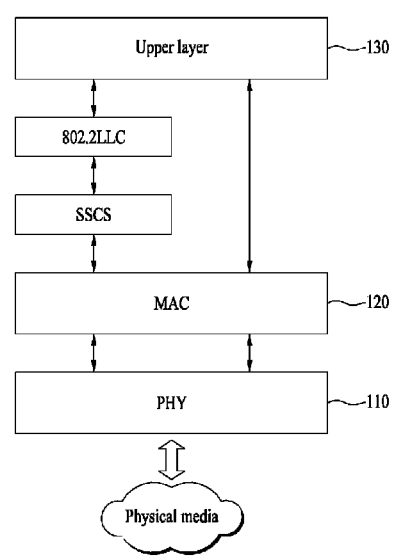
FIG. 2 is a diagram of a structure of a protocol stack in IEEE 802.15.4 system.

FIG. 2 is a diagram of a structure of a protocol stack in IEEE 802.15.4 system, which is an example of an LR-WPAN system.

Referring to FIG. 2, the protocol stack consists of a PHY (physical) layer, a MAC layer (medium access control layer), and an upper layer.

The PHY layer includes a RF transmitter/receiver and a related control mechanism. The PHY layer can provide a PHY data service to transmit/receive PHY PDU (protocol data units) and a PHY management service to manage the PHY layer on a physical channel.

The MAC layer provides an access to a physical channel to transmit a data. The MAC layer can provide a MAC data service to transmit/receive MAC PDU (protocol data units) and a MAC management service to manage the MAC layer via the physical layer. The MAC layer can perform such a function as a beacon management, channel access, GTS management, frame confirmation, a security function, and the like.

The upper layer consists of a network layer and an application layer. The network layer provides such a function as a network configuration, processing, message routing, and the like. The application layer provides a function for which the device is aiming. As an example, IEEE 802.15.4 device 100 may function as an RFD (reduced function device), an FFD (full function device), or a coordinator according to a type of program installed in the device, i.e., the type of program for processing a data of the application layer.

Figure 3A:
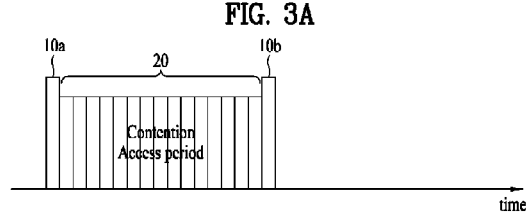
FIG. 3 is a diagram of a superframe structure used in IEEE 802.15.4 system.
Figure 3B:
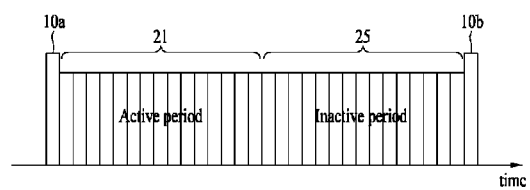
Figures 3C, 4:
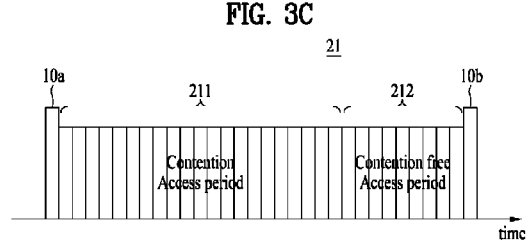
FIG. 4 is a diagram of a beacon frame structure used in IEEE 802.15.4 system.

FIG. 3a to FIG. 3c is a diagram of a superframe structure used in IEEE 802.15.4 system, which is an example of the LR-WPAN system.

The superframe structure used in the LR-WPAN system can be determined by a coordinator. The coordinator transmits a super frame configured with a beacon frame positioned at a first slot. In case of not using the superframe, the coordinator does not perform a beacon transmission.

Meanwhile, devices intending to transmit a data wait for a beacon frame transmitted by the coordinator. If the beacon frame is received, the devices perform synchronization to the superframe structure. The beacon frame synchronizes devices participating in a PAN, which is established by the coordinator, identifies the PAN, and is used to indicate the structure of the superframe.

In the following description, the superframe structure capable of being used to transmit/receive a data between devices is explained with reference to FIG. 3.

In order to transmit/receive a data using the superframe, devices in the LR-WPAN system competitively perform a media access. Yet, in case that the coordinator participating in the WPAN assigns a time slot to specific devices using the superframe, a device to which the time slot is assigned can transmit/receive a data without conflicting with different devices. In particular, according to the superframe structure determined by the coordinator, the devices participating in the WPAN can competitively or noncompetitively perform the media access to transmit/receive a data.

FIG. 3a depicts a superframe structure for indicating a contention access period. Referring to FIG. 3a, the superframe in the LR-WPAN system is configured in a form that a plurality of time slots 20 (e.g., 16) to transmit a data are included between beacon frames (10a to 10b, etc.) transmitted by the coordinator. In case of using the aforementioned type of superframe structure, the devices participated in the WPAN can transmit a data frame to the coordinator using the time slots in the superframe based on a CSMA-CA (carrier sense multiple access/collision avoidance) scheme.

FIG. 3b depicts a superframe structure including an active period and an inactive period. Referring to FIG. 3b, the superframe in the LR-WPAN system can be configured to include the active period 21 and the inactive period 25 between the beacon frames (10a to 10b, etc.).

The active period 21 is a period of which a data transmission/reception is performed between the devices. The active period 21 consists of time slots for frames used to transmit/receive a data. Yet, the inactive period 25 indicates a period where a data transmission and reception between the devices is not performed.

During the inactive period 25, the coordinator can enter into a low-power mode.

A ratio of the active period 21 and the inactive period can be called a duty cycle. A value of the duty cycle can be adjusted in consideration of a requirement for a low-power operation of the LR-WPAN system and a requirement for co-existence between communication schemes using an identical physical transport channel.

FIG. 3c depicts a structure of an active period. Referring to FIG. 3c, the active period 21 used to transmit/receive a data can be configured to include a contention access period (hereinafter abbreviate CAP) 211 and a contention free period (hereinafter abbreviate CFA) 212.

The CAP 211 is configured with time slots used for the devices participated in the WPAN to transmit a data frame. Hence, a device intends to perform a communication using the time slots belong to the CAP 211 between the two beacon frames 10a and 10b is in competition with a different device in using the CSMA-CA scheme.

The CFP 212 is configured with GTS (guaranteed time slots), which are assigned for a specific device to transmit a data frame. The GTS can be used for a low-latency application program in the specific device or an application program requiring a specific transmission bandwidth in the specific device.

For instance, in IEEE 802.15.4 standard corresponding to an example of the LR-WPAN, the CFP 212 is positioned after the CAP 212 in the superframe and can be configured to include up to maximum 7 GTSs. And, the CFP 212 can be configured that a plurality of GTSs are assigned for a single device.

The coordinator determines each of the GTSs in the CFP 212 assigned to a device. GTS assignment information of the CFP 212, which is determined by the coordinator, can be transmitted in a manner of being included in a beacon frame 10a, which is the first slot of the superframe.

FIG. 4 is a diagram of a beacon frame structure used in IEEE 802.15.4 system.

Content of each field included in a beacon frame follows the content defined by IEEE 802.15.4. In particular, assignment content for each GTS is configured with a GTS descriptor form by the WPAN coordinator. GTS descriptors are included in a GTS list field of a beacon.

Figure 5:
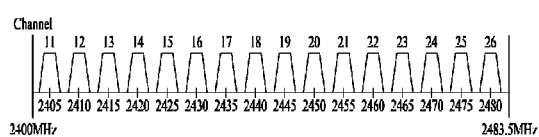
FIG. 5 is a diagram of a channel arrangement of IEEE 802.15.4 system.

FIG. 5 is a diagram of a channel arrangement of IEEE 802.15.4 system.

Referring to FIG. 5, IEEE 802.15.4 system operating in 2400 MHz band has a channel spacing of 5 MHz.

The MBAN system based on the IEEE 802.15.4 system uses 2360~2390 MHz band and 2390~2400 MHz band. 2360~2390 MHz band is used for an MBAN user equipment to receive a channel from a MBAN coordinator and to operate. (Hereinafter 'MBAN PAN coordinator', 'PAN coordinator', and 'MBAN coordinator' are used as a same meaning.) 2390~2400 MHz band is used when the MBAN user equipment is not able to receive information on an MBAN channel from the MBAN coordinator any more or the MBAN user equipment or the coordinator operates at the outside of the healthcare facility. And, 2390~2400 MHz band can be used as a basic channel band of an MBAN system.

Figure 6:
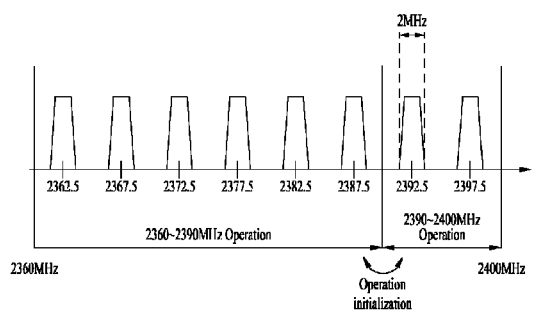
FIG. 6 is a diagram for an example of a channel arrangement of an MBAN system.

FIG. 6 is a diagram for an example of a channel arrangement of an MBAN system.

FIG. 6 depicts available channels of the MBAN in 2360~2400 MHz band. The MBAN user equipment operating in the aforementioned band may have a chance to change from a channel in 2360~2390 MHz band to a channel in 2390~2400 MHz band and vice versa. For instance, in case of using the channel in 2360~2390 MHz band by a user (primary user) of a wireless communication system having a priority for the corresponding band except the MBAN system, the user equipment of the MBAN system should switch an operation channel to a channel of 2390~2400 MHz band. In this case, the MBAN user equipment performs an operation defaulting and switches a channel.

In the following description, a method of a channel switching between 2360~2390 MHz band and 2390~2400 MHz band is described.

FIG. 7a and FIG. 7b is a flowchart for a method of a channel switching, which is switched by a user equipment according to embodiment of the present invention.

In the embodiment of the present invention, the user equipment is a user equipment of a WPAN. In particular, the user equipment may correspond to a user equipment of an MBAN.

FIG. 7a is an example that the user equipment operating in 2360 MHz 2390 MHz band switches an operation channel to a channel in 2390~2400 MHz band.

A coordinator of an MBAN, i.e., a first PAN coordinator 201 and an MBNA user equipment 100 establish an association via a channel among channels in 2360~2390 MHz band and transceive a data with each other [S710]. In this case, it may have a case that the user equipment 100 should switch a using channel to a channel of a different frequency band. For instance, in case that a primary user of a wireless communication system except the MBAN system should use the 2360~2390 MHz band or in case that the user equipment moves to an external of a designated area (e.g., in case of moving to an outside of a healthcare facility), the user equipment 100 switches to a channel of 2390~2400 MHz band. And then, the user equipment should transceive a data with a PAN coordinator of the changed channel, i.e., a second PAN coordinator 202.

In this case, the 2360~2390 MHz band and the 2390~2400 MHz band are called a first frequency band and a second frequency band, respectively. As mentioned earlier, the first frequency band and the second frequency band are the frequency bands classified on the basis of whether the user equipment can preferentially use the corresponding frequency band.

Information on a channel status of each frequency band, in particular, the information for indicating that which channels of the 2360~2390 MHz band of the MBAN (the first frequency band) and the 2390~2400 MHz band (the second frequency band) are available and when the channels are available can be collected and managed by a controller that controls a plurality of PAN coordinators.

The controller can be configured in a manner of including a DB for storing and managing the channel status of each frequency band and an MBAN control point for managing the DB.

If the aforementioned channel switching is required, information on a usage of each channel of a different frequency band (the second frequency band) to be switched is delivered to the first PAN coordinator 201 from the controller.

Having received information on a switching to the second frequency band from the controller or the MBAN control point, the first PAN coordinator 201 transmits channel switching information to the user equipment 100 based on the information on the switching [S730]. The channel switching information may include a channel number of the second frequency band, a switching time, a PAN ID of the second frequency band to which the user equipment switches, and the like. Regarding this, it shall be described in detail in FIG. 8.

The user equipment can reduce time for scanning channels in the second frequency band and power consumption by using channel information of the second frequency band to which the user equipment switches. And, if a plurality of PANs exist in the second frequency band or if a PAN not capable of knowing its ID exists in the second frequency band, the user equipment can promptly perform a channel switching using a PAN ID information. The PAN ID included in the switching information can be determined by the PAN coordinator in consideration of an anticipated moving situation of the user equipment, a PAN arrangement of a surrounding, and the like.

The channel switching information can be transmitted to the user equipment 100 by a broadcast or a unicast scheme. The broadcast scheme may be performed by a scheme of transmitting the channel switching information in a manner of including the channel switching information in a beacon frame. The unicast scheme can be performed by separately defining a command for a channel switching or a frame. For instance, the command or the frame defined for the channel switching may have a name of a channel switching notification command, a channel switching parameter frame, and the like.

Having received the channel switching information from the first PAN coordinator 201, the user equipment 100 performs a channel switching based on the channel switching information and establishes an association with a second PAN coordinator 202 [S704]. After establishing the association, the user equipment 100 transceives a data with the second PAN coordinator 202.

After the user equipment has performed the channel switching from the first frequency band to the second frequency band, continuously using a channel of the second frequency band may give a load to the second frequency band. Hence, it is preferable to switch back to the first frequency band after a prescribed time. To this end, the switching information may further include a time of switching back to the first frequency band after switching to the second frequency band and channel information. Regarding this, it shall be described in detail in FIG. 8.

It is not necessary for the user equipment to periodically scan all channels of the first frequency band to find out an original network by using the time and channel information. By using the time and channel information, power consumption of the user equipment can be reduced and a radio resource can be more efficiently used.

FIG. 7b is a different embodiment that a user equipment operating in 2360 MHz band switches an operation channel to a channel of 2390~2400 MHz band.

S710' is identical to the S710 explained in FIG. 7a. Subsequently, the user equipment 100 makes a request for channel switching information to the first PAN coordinator 201 [S720']. If a period of a beacon is very long or if the user equipment fails to receive the channel switching information, since it is necessary to update a channel switching parameter by a request of the user equipment, it may necessary to have the request. A parameter related to the channel switching information request is described in detail in FIG. 9.

S730' to S740' are identical to the S730 to S740 explained in FIG. 7a.

A Different Embodiment of Switching an Operation Channel Switched by a User Equipment In FIG. 7a and FIG. 7b, a channel switching between 2360~2390 MHz band and 2390~2400 MHz band is explained. Yet, unlike the aforementioned embodiment, the user equipment can resume an operation in a manner of switching to a different channel in an identical frequency band.

For instance, in case that a primary user uses a part of channel of the channels in 2360~2390 MHz band only, user equipments used to transmit/receive a data on the corresponding channel can switch to a different channel in an identical band. In this case, as mentioned earlier in the step S730 and S730' in FIG. 7 and FIG. 7b, the PAN coordinator can transmit channel switching information to the user equipments of the corresponding channel. The channel switching information can include a channel number to which the user equipments switch, a switching time, a PAN ID existing in a channel to switch, and the like.

FIG. 8 is a diagram of channel switching information according to one embodiment of the present invention.

The channel switching information can include a channel number of the second frequency band to which the user equipment switches, a switching time, a PAN ID of the second frequency band to switch, and the like.

FIG. 8a is an example of a broadcast message including the channel switching information. In this case, in case of using a beacon frame as the broadcast message, the beacon frame can include a time for switching to a different frequency band (e.g., 'escape time' field) 831, a channel of a different frequency band to switch (e.g., 'escape channel' field) 832, a time for switching back to an original frequency band (e.g., 'recovery time' field) 833, and information on a channel of an original frequency band to switch back (e.g., 'recovery channel' field) 834.

Figure 8B:
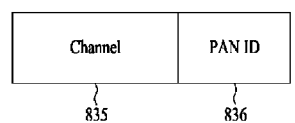

In this case, the beacon frame may further include identification information (e.g., 'PAN ID' field) of a PAN existing in a channel of the second frequency band to switch. The exemplified 'PAN ID' field 836 is depicted in FIG. 8b.

The user equipment can reduce time for scanning a channel in a different frequency band by using the identification information of the PAN. And, if a plurality of PANs exist in the different frequency band or if a PAN not capable of knowing its ID exists in the different frequency band, the user equipment can promptly perform a channel switching using identification information of the PAN. The identification information of the PAN can be determined by the PAN coordinator in consideration of an anticipated moving situation of the user equipment, a PAN arrangement of a surrounding, and the like.

The exemplified beacon frame can be generated by a coordinator, which received information on a switching to a different frequency band from the MBAN controller, the MBAN control point, and the like.

Figure 8C:
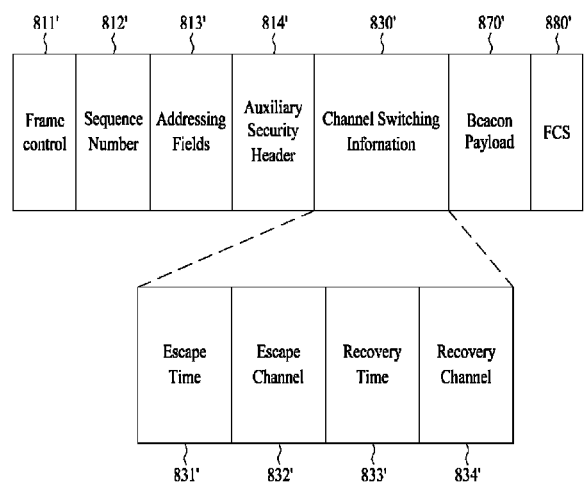

FIG. 8c is an example of a unicast message including the channel switching information. The unicast message can have such a name as a channel switching parameter frame and the like.

Similar to the content described in FIG. 8a, the unicast message depicted in FIG. 8c can include a time for switching to a different frequency band (e.g., 'escape time' field) 831, a channel of a different frequency band to switch (e.g., 'escape channel' field) 832, a time for switching back to an original frequency band (e.g., 'recovery time' field) 833, and information on a channel of an original frequency band to switch back (e.g., 'recovery channel' field) 834.

And, the unicast message may further include identification information (e.g., 'PAN ID' field) of a PAN existing in a channel of the second frequency band to switch.

Figure 8D:
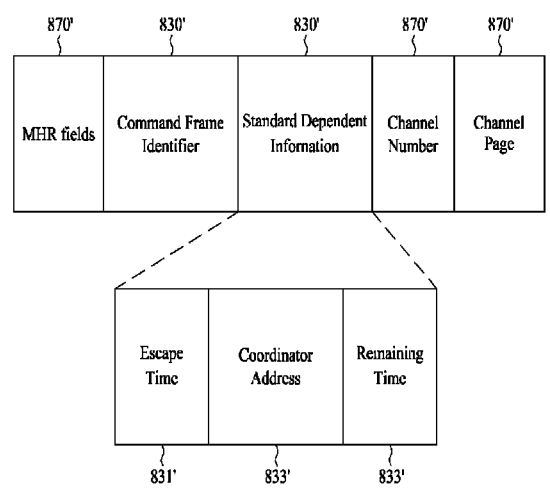

FIG. 8d is a different example of the unicast message including the channel switching information. The unicast message can have such a name as a channel switch notification command and the like. Similar to the content described in FIG. 8a, the unicast message depicted in FIG. 8d can include a time for switching to a different frequency band (e.g., 'remaining field' field) and information on a channel (e.g., 'channel number' field) of a different frequency band to switch.

And, the unicast command may further include identification information (e.g., 'new PAN ID' field) of a PAN existing in the second frequency band to switch and device address information (e.g., 'coordinator address' filed).

Figure 9:
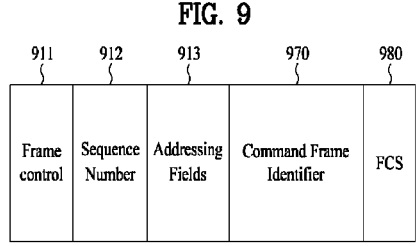
FIG. 9 is a diagram for one example of a channel switching information request message according to embodiment of the present invention.

FIG. 9 is a diagram for one example of a channel switching information request message according to embodiment of the present invention.

As mentioned earlier in FIG. 7, If a period of a beacon frame is very long or if the user equipment fails to receive the channel switching information, since it is necessary to update a channel switching parameter by a request of the user equipment, it may necessary to have the channel switching information request message.

In an example of FIG. 9, a command frame identifier (e.g., 'command frame identifier' field) 970 can indicate a message for requesting the channel switching information requested by the user equipment in a manner of defining the command frame identifier with a prescribed value. For instance, the message for requesting the channel switching information can be indicated by configuring a value of the 'command frame identifier' filed to '0x0a'.

Having received the channel switching information request message, the PAN coordinator can transmit channel switching information to the user equipment using the broadcast message or the unicast message described in FIG. 8.

Figure 10:
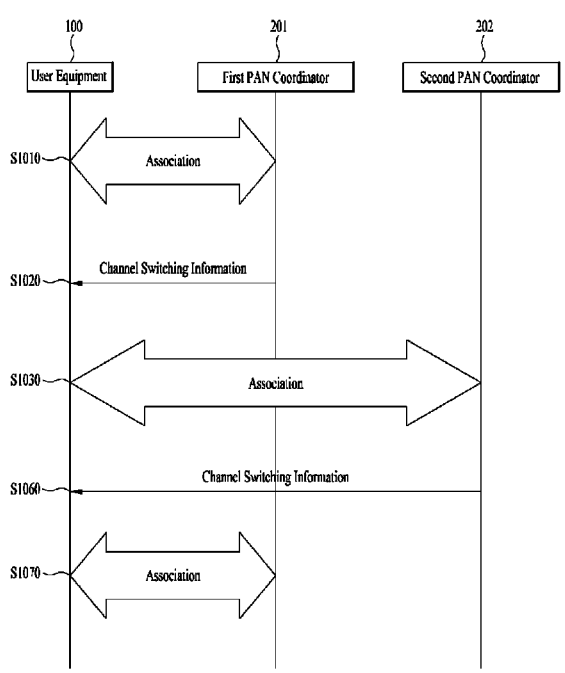
FIG. 10 is a flowchart for a method of channel switching, which is switched by a user equipment according to a different embodiment of the present invention.

FIG. 10 is a flowchart for a method of channel switching, which is switched by a user equipment according to a different embodiment of the present invention.

FIG. 10 depicts a process of switching back to 2360~2390 MHz band after a user equipment operating in 2360~2390 MHz band has switched an operation channel to a channel of 2390~2400 MHz band.

In case that the user equipment has performed a channel switching from 2360~2390 MHz band to 2390~2400 MHz band, continuously using a channel of the 2390~2400 MHz band may give a load to the channel of the 2390~2400 MHz band. Hence, it is preferable to switch back to the 2360~2390 MHz band after a prescribed time. Yet, in order to establish an association to a network of the previously used 2360~2390 MHz band, it is necessary to scan all channels of the band on every prescribed time. The present embodiment proposes a method of eliminating an unnecessary operation in a manner of delivering needed information to the user equipment in advance and a method of reducing power consumption for the aforementioned process.

S1010 to S1040 in FIG. 10 are identical to S710 to S740 in FIG. 7a.

Subsequently, a situation of switching back to the first frequency band from the second frequency band may occur. An example of the situation of switching back may correspond to a case that a use of a primary user for the first frequency band ends.

In case that the channel switching is available, information on the use of each channel of the original frequency band (first frequency band) can be delivered to the second PAN coordinator 202 from the controller.

Having received the channel information of the first frequency band from the controller and the like, the second PAN coordinator 202 transmits channel switching information to the user equipment 100 based on the channel information [S1060]. In this case, the second PAN coordinator 202 may transmit the channel switching information in response to an information transmission request of the user equipment 100. The information transmission request of the user equipment 100 is described in detail in FIG. 11.

The channel switching information can include a channel number of the first frequency band to which the user equipment switches, a time for switching, a beacon transmission time on a channel of the first frequency band, a PAN ID, and the like. Regarding this, it shall be described in detail in FIG. 11.

The user equipment 100 can reduce time for scanning a channel of the first frequency band and power consumption using the channel information of the first frequency band to switch. And, if a plurality of PANs exist in the first frequency band or if a PAN not capable of knowing its ID exists in the first frequency band, the user equipment can promptly perform a channel switching using a PAN ID information. The PAN ID included in the switching information can be determined by the PAN coordinator in consideration of an anticipated moving situation of the user equipment, a PAN arrangement of a surrounding, and the like.

The channel switching information can be transmitted to the user equipment 100 by a broadcast or a unicast scheme. The broadcast scheme may be performed by a scheme of transmitting the channel switching information in a manner of including the channel switching information in a beacon frame. The unicast scheme can be performed by separately defining a command for a channel switching or a frame. For instance, the command or the frame defined for the channel switching may have a name of a channel switching notification command, a channel switching parameter response frame, and the like.

Detailed explanation on the broadcast or unicast message is described in FIG. 12.

Having received the channel switching information from the second PAN coordinator 202, the user equipment 100 perform a channel switching based on the channel switching information and establishes an association with a first PAN coordinator 201 [S1070]. After establishing the association, the user equipment 100 transceives a data with the first PAN coordinator 201.

Figure 11:
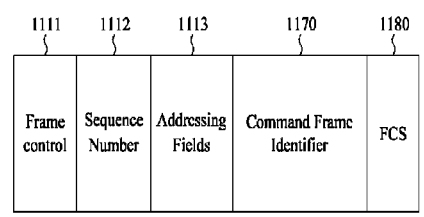
FIG. 11 is a diagram for one example of a channel switching information request message according to a different embodiment of the present invention.

FIG. 11 is a diagram for one example of a channel switching information request message according to a different embodiment of the present invention.

As mentioned earlier in FIG. 10, a situation of switching back to the first frequency band from the second frequency band may occur. In this case, the channel switching information request message may be required.

Referring to an example of FIG. 11, a command frame identifier (e.g., 'command frame identifier' field) 1170 can indicate a message for requesting the channel switching information requested by the user equipment in a manner of defining the command frame identifier with a prescribed value. For instance, the message for requesting the channel switching information can be indicated by configuring a value of the 'command frame identifier' filed to '0x0a'.

Having received the channel switching information request message, the PAN coordinator can transmit channel switching information to the user equipment using the broadcast message or the unicast message described in FIG. 12.

FIG. 12 is a diagram of a delivery message of channel switching information according to a different embodiment of the present invention.

As mentioned earlier in FIG. 10, the channel switching information can include a channel number of the first frequency band to which the user equipment switches, a time for switching, a PAN ID of the first frequency band, a beacon transmission time on a channel of the first frequency band, and the like.

FIG. 12*a* is an example of a broadcast message including the channel switching information. In this case, if a beacon frame is used as the broadcast message, the beacon frame can include information on a time for switching to the first frequency band (e.g., 'remain time' field) 1231, a channel of the first frequency band to switch (e.g., 'recommend channel' field) 1232, a beacon transmission time in a channel of the first frequency band (e.g., 'TBTT' field) 1233.

In this case, the beacon frame may further include identifier information (e.g., 'PAN ID' field) of a PAN existing in the PAN of the first frequency band to switch.

The exemplified beacon frame can be generated by a second coordinator, which has received information on a switching to the first frequency band from the MBAN controller, the MBAN control point, and the like. In this case, the second coordinator can transmit an address of a user equipment requiring a channel switching in a manner of including the address in the beacon frame.

Figure 12B:
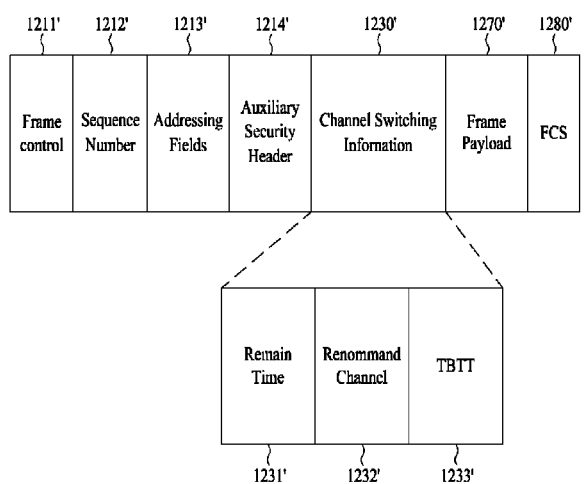

FIG. 12*b* is an example of a unicast message including the channel switching information. The unicast message can have such a name as a channel switching parameter response frame and the like.

As mentioned earlier in FIG. 12*a*, the unicast message depicted in FIG. 12*b* can include information on a time for switching to the first frequency band (e.g., 'remain time' field) 1231', a channel of the first frequency band to switch (e.g., 'recommend channel' field) 1232', a beacon transmission time in a channel of the first frequency band (e.g., 'TBTT' field) 1233'.

And, the unicast frame may further include identifier information (e.g., 'PAN ID' field) of a PAN existing in the PAN of the first frequency band to switch.

Referring to an example of FIG. 12*b*, a command frame identifier (e.g., 'command frame identifier' field) can indicate a message for responding to the channel switching information request of the user equipment in a manner of defining the command frame identifier with a prescribed value. For instance, the message for responding to the channel switching information request can be indicated by configuring a value of the 'command frame identifier' filed to '0x0b'.

Figure 13:
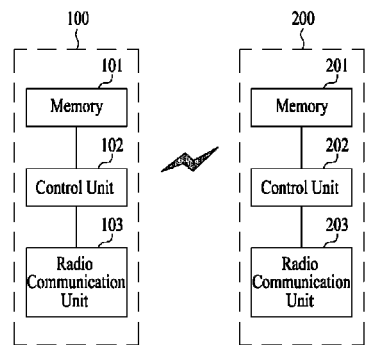
FIG. 13 is a block diagram of a user equipment and a PAN coordinator according to embodiment of the present invention.

FIG. 13 is a block diagram of a user equipment and a PAN coordinator according to embodiment of the present invention.

The user equipment 100 can consist of a memory 101, a control unit 102, and a radio communication unit 103.

The memory 101 can store methods proposed by the present specification. And, the memory 101 can store channel switching information received according to a control of the control unit 102.

The control unit 102 controls an overall operation of the user equipment, the memory 101 and the radio communication unit 103. The control unit 102 can receive information on a channel switching to a different frequency band from a PAN coordinator. In this case, the information on the channel switching can include a time for channel switching, a channel to be switched, a PAN ID, and the like.

The control unit 102 can control a channel switching based on the received information on the channel switching.

The radio communication unit 103 can switch an operation channel in an MBAN system according to a control of the control unit 102.

A PAN coordinator 200 can consist of a memory 201, a control unit 202, and a radio communication unit 203.

The memory 201 can store methods proposed by the present specification. And, the memory 201 can store information on a use of channels of an MBAN frequency band according to a control of the control unit 202. In particular, the memory can store information on a usage of each of the channels, available time of each of the channels, and the like.

The control unit 102 controls an overall operation of the PAN coordinator 200, the memory 101, and the radio communication unit 103. The control unit 102 can receive information on a use of each channel of the MBAN frequency band from an MBAN controller. The control unit 102 generates information on a channel switching of user equipments based on the received information and can transmit the generated information to a plurality of user equipments. In this case, the information on the channel switching can include a time for channel switching, a channel to be switched, a PAN ID, and the like.

The control unit 102 can transmit the information on the channel switching by a broadcast scheme of a unicast scheme. In case of transmitting by the broadcast scheme, the control unit 102 can transmit the information on the channel switching in a manner of including the information in a beacon frame.

The radio communication unit 203 can perform a communication with a user equipment on a designated channel according to a control of the control unit 102. And, the radio communication unit 203 can transmit a beacon and command frames to a physical channel according to a control of the control unit 102.

The above-described embodiments may correspond to combinations of elements and features of the present invention in prescribed forms. And, it may be able to consider that the respective elements or features may be selective unless they are explicitly mentioned. Each of the elements or features may be implemented in a form failing to be combined with other elements or features. Moreover, it may be able to implement an embodiment of the present invention by combining elements and/or features together in part. A sequence of operations explained for each embodiment of the present invention may be modified. Some configurations or features of one embodiment may be included in another embodiment or can be substituted for corresponding configurations or features of another embodiment. And, it is apparently understandable that a new embodiment may be configured by combining claims failing to have relation of explicit citation in the appended claims together or may be included as new claims by amendment after filing an application.

While the present invention has been described and illustrated herein with reference to the preferred embodiments thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

What is claimed is:

1. A method of switching an operation channel by a user equipment in a wireless personal area network (WPAN) system, the method comprising:
   receiving a beacon frame including change information on a channel switching related with a first frequency band and a second frequency band, the change information comprising a first field related to a remain time for channel switching and a second field related to time value of the beacon frame; and
   performing a channel switching procedure in a range of 2360 MHz and 2400 MHz.

2. The method of claim 1, wherein the channel switching occurs when a different wireless communication system uses the first frequency band or the user equipment moves to an outside of a designated area.

3. The method of claim 1, wherein the change information further comprises a PAN ID of the PAN coordinator operating on a channel of the second frequency band to switch.

4. The method of claim 1, further comprising requesting the change information to a PAN coordinator of the first frequency band.

5. A user equipment, comprising:
   a control unit configured to control a channel switching of the user equipment; and
   a radio communication unit configured to communicate with a PAN (personal area network) coordinator according to a control of the control unit,
   wherein the control unit is further configured to:
      receive a beacon frame including change information on a channel switching related with a first frequency band and a second frequency band, the change information comprising:
         a first field related to a remain time for channel switching, and
         a second field related to time value of the beacon frame, and
      perform a channel switching procedure in a range of 2360 MHz and 2400 MHz.

* * * * *